United States Patent
Kuroda et al.

(10) Patent No.: US 9,952,606 B2
(45) Date of Patent: Apr. 24, 2018

(54) AUTOMATIC PH ADJUSTMENT DEVICE

(71) Applicants: SYSTEM INSTRUMENTS CO., LTD., Hachioji-shi, Tokyo (JP); NATIONAL INSTITUTE OF ADVANCED INDUSTRIAL SCIENCE AND TECHNOLOGY, Tokyo (JP)

(72) Inventors: Toshiharu Kuroda, Tokyo (JP); Michio Horiuchi, Tokyo (JP); Yanbei Zhu, Ibaraki (JP); Koichi Chiba, Ibaraki (JP)

(73) Assignees: SYSTEM INSTRUMENTS CO., LTD., Tokyo (JP); NATIONAL INSTITUTE OF ADVANCED INDUSTRIAL SCIENCE AND TECHNOLOGY, Tokyo (JP)

( * ) Notice: Subject to any disclaimer, the term of this patent is extended or adjusted under 35 U.S.C. 154(b) by 0 days.

(21) Appl. No.: 14/911,116

(22) PCT Filed: Jul. 15, 2014

(86) PCT No.: PCT/JP2014/068819
§ 371 (c)(1),
(2) Date: Feb. 9, 2016

(87) PCT Pub. No.: WO2015/029624
PCT Pub. Date: Mar. 5, 2015

(65) Prior Publication Data
US 2016/0195880 A1 Jul. 7, 2016

(30) Foreign Application Priority Data

Aug. 30, 2013 (JP) ................. 2013-179817

(51) Int. Cl.
| | |
|---|---|
| *G05D 21/00* | (2006.01) |
| *B01L 3/00* | (2006.01) |
| *G01N 21/80* | (2006.01) |
| *G05D 21/02* | (2006.01) |
| *B05B 15/00* | (2018.01) |

(52) U.S. Cl.
CPC .............. *G05D 21/00* (2013.01); *B01L 3/502* (2013.01); *B05B 15/00* (2013.01); *G01N 21/80* (2013.01);
(Continued)

(58) Field of Classification Search
CPC ....................................................... G01N 21/80
See application file for complete search history.

(56) References Cited

U.S. PATENT DOCUMENTS

| | | |
|---|---|---|
| 2003/0159652 A1 | 8/2003 | Yang et al. |
| 2008/0252877 A1 | 10/2008 | Kok et al. |

(Continued)

FOREIGN PATENT DOCUMENTS

| | | | |
|---|---|---|---|
| JP | H01-165938 A | | 6/1989 |
| JP | 11285654 A | * | 10/1999 |

(Continued)

OTHER PUBLICATIONS

Oct. 14, 2014 Search Report issued in International Patent Application No. PCT/JP2014/068819.

(Continued)

*Primary Examiner* — P. Kathryn Wright
(74) *Attorney, Agent, or Firm* — Oliff PLC

(57) ABSTRACT

In an embodiment, control is performed to operate a three-way valve in accordance with a reaching ratio of pH adjustment. When process of certain steps is performed, bubbles of ammonia generated in a nebulizer can be extruded by air so as to be injected from an injection port together with aqua ammonia remaining in the nebulizer. Therefore, the pH adjustment can be performed while a large amount of bubbles of ammonia are prevented from being generated in the nebulizer.

2 Claims, 3 Drawing Sheets

Figure 1:
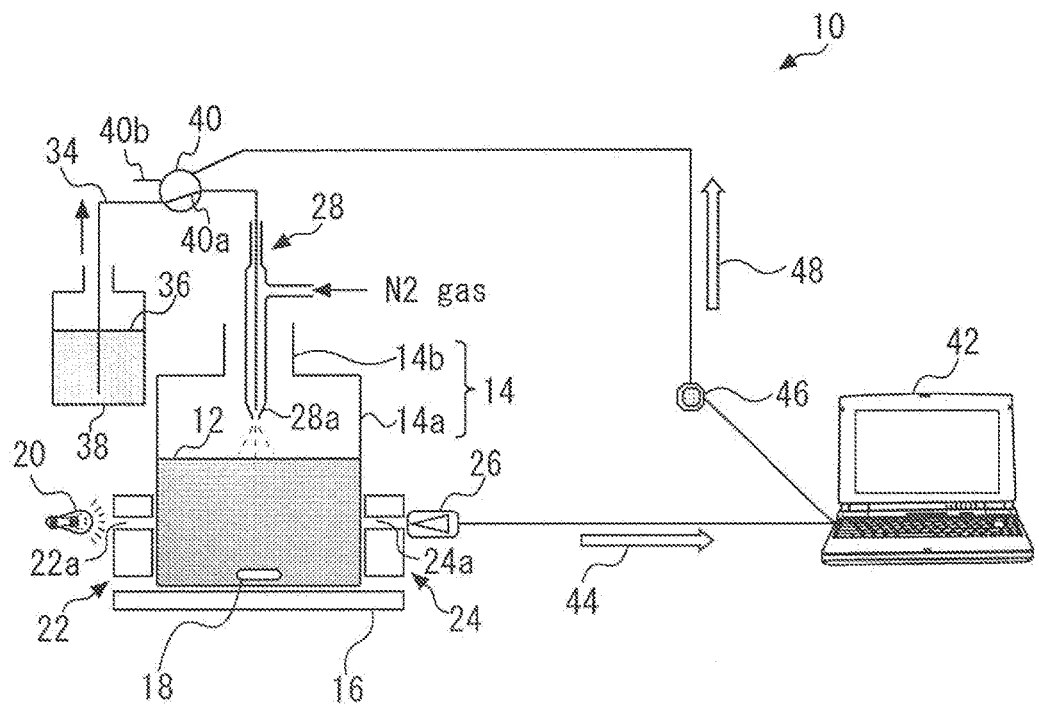
Figure 2:
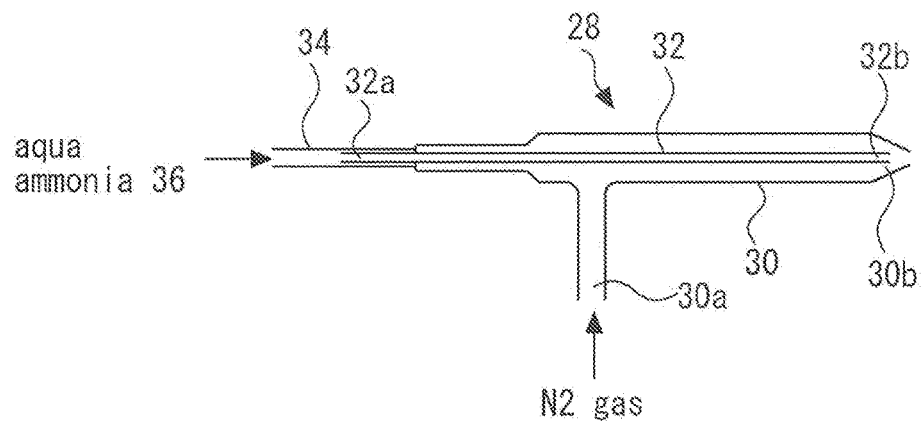

(52) U.S. Cl.
CPC .......... *G05D 21/02* (2013.01); *B01L 2200/14* (2013.01); *B01L 2300/06* (2013.01); *B01L 2300/0627* (2013.01); *B01L 2400/0622* (2013.01)

(56) References Cited

U.S. PATENT DOCUMENTS

2009/0217947 A1  9/2009  Wiederin et al.
2009/0301231 A1  12/2009  Wang et al.

FOREIGN PATENT DOCUMENTS

| JP | 2003-177093 A | 6/2003 |
| JP | 2005-195412 A | 7/2005 |
| WO | 2013/140560 A1 | 9/2013 |

OTHER PUBLICATIONS

Zhu, Yanbei et al. "Development of Solid-Phase Extraction Fully Automatic Processing System for Separation and Concentration of Trace Elements". The Oceanographic Society of Japan 2011 Spring Meeting, Abstracts, pp. 159.

Zhu, Yanbei et al. "Development of an Automatic pH-Adjustment System for Solid Phase Extraction Prior to the Determination of Rees in Seawater by ICP-MS". J. Anal. At. Spectrum, 2013, vol. 28, pp. 883-889.

Apr. 3, 2017 Extended European Search Report issued in Application No. 14840863.6.

Feb. 8, 2018 Office Action issued in European Application No. 14840863.3.

* cited by examiner

AUTOMATIC PH ADJUSTMENT DEVICE

TECHNICAL FIELD

The present invention relates to an automatic pH adjustment device and, more particularly, to an automatic pH adjustment device used for pH adjustment as a pretreatment of solid-phase extraction.

BACKGROUND ART

Analysis of trace elements including heavy metals has been performed for material circulation research in the ocean, water quality testing of tap water, water quality testing of lake water and river water, and the like. At the time of analysis of trace elements, for the purpose of separating the trace elements from interference components or for the purpose of improving the sensitivity of analysis, there may be required the separation and concentration of the trace elements based on solid-phase extraction using a chelating resin, and the like. When the separation and concentration are performed, it is required to adjust in advance a liquid sample to optimum pH conditions.

Further, in view of the purposes of analysis of trace elements, it is desirable that contamination factors in the pH adjustment are removed as much as possible. In this regard, the present inventors have developed an indirect measurement method using color change characteristics of a pH indicator (Non Patent Literature 1). In the indirect measurement method, an optical sensor is used as a pH measuring instrument, and hence contamination due to contact between the measuring instrument and the sample can be eliminated. Further, in the indirect measurement method, methyl yellow, methyl orange or methyl red is used as the pH indicator, and ammonia is used as a pH adjusting liquid. In the indicator and the adjusting liquid which are used for the indirect measurement method, contamination due to the indicator and the adjusting liquid can be eliminated by using a high purity reagent in which the amount of metal components is suppressed to be sufficiently small.

CITATION LIST

Patent Literature

Patent Literature 1: Japanese Patent Laid-Open No. 2003-177093

Non Patent Literature

Non Patent Literature 1: Zhu Yanbei, Asakai Toshiaki, Chiba Koichi, Ono Mitsumasa, Kuroda Toshiharu, Nara Tomio, "Development of solid-phase extraction fully automatic processing system for separation and concentration of trace elements", the Oceanographic Society of Japan 2011 Spring Meeting, Abstracts, Mar. 14, 2011, pp. 159

SUMMARY OF INVENTION

Technical Problem

In addition to the disclosure of Non Patent Literature 1, the present inventors have studied to adopt a nebulizer in a pH adjusting liquid supply device. This is because, when the nebulizer is used, a pH adjusting liquid can be sucked and atomized by a carrier gas, as a result of which, as compared with the case where the pH adjusting liquid is supplied in a liquid state, the deviation of the hydrogen concentration distribution in the sample is reduced, which allows the pH adjusting liquid to stably reach the adjustment target pH.

However, when aqua ammonia as the pH adjusting liquid is injected from the nebulizer, there is a problem that bubbles are generated in the nebulizer. This is because ammonia dissolved in the pH adjusting liquid is vaporized by a negative pressure action generated when the carrier gas is injected from the nebulizer. When a large amount of ammonia bubbles are generated, there is a problem that the continuous injection cannot be performed due to the affect of the surface tension of the bubbles, and thereby the stable pH adjustment is hindered.

The present invention has been made in view of the above-described problem. That is, an object of the present invention is to provide an automatic pH adjustment device capable of stably performing pH adjustment even when a nebulizer is adopted in a pH adjustment liquid supply device.

Means for Solving the Problem

To achieve the above described object, a first aspect of the present invention is an automatic pH adjustment device comprising:

a container that accommodates a liquid sample to which a pH indicator is added, color of the pH indicator changes in accordance with pH;

an adjusting liquid bottle that stores aqua ammonia or carbonated water used as a pH adjusting liquid;

a nebulizer that is provided with an injection port disposed to face a sample liquid surface in the container and injects from the injection port the pH adjusting liquid stored in the adjusting liquid bottle and atomized by carrier gas;

a multi-way valve that is disposed between the nebulizer and the adjusting liquid bottle and performs switching between a liquid injection state in which the nebulizer is allowed to communicate with the adjusting liquid bottle to inject the pH adjusting liquid from the injection port, and an air injection state in which the nebulizer is allowed to communicate with outer air to inject air from the injection port;

a detecting device that detects the intensity of light radiated from the outside of the container and transmitted through the container; and a control device that switches the communication state of the multi-way valve on the basis of the intensity of light detected by the detecting device.

A second aspect of the present invention is the automatic pH adjustment device according to the first aspect, wherein the detecting device is configured to detect the intensity of light of a specific wavelength absorbed by the pH indicator if the sample is adjusted to target pH and the intensity of light of a reference wavelength not absorbed by the pH indicator if the sample is adjusted to the target pH; and the control device is configured to calculate an intensity ratio from the intensity of light of the specific wavelength detected by the detection device and the intensity of light of the reference wavelength detected by the detection device, and is configured to switch the communication state of the multi-way valve by comparing the calculated intensity ratio with a target intensity ratio set in accordance with the target pH.

The third aspect of the present invention is the automatic pH adjustment device according to the second aspect, wherein the control device is also configured to reduce the period of the liquid injection state as the ratio approaches 1, when the ratio of the calculated intensity ratio with respect to the target intensity ratio is in a predetermined range including 1.

Advantageous Effects of Invention

In the first aspect of the present invention, the communication state of the multi-way valve can be switched on the basis of the intensity of light transmitted through the container containing the liquid sample. The switching of the communication state is performed between the state in which the nebulizer communicates with the adjustment liquid bottle (liquid injection state) and the state in which the nebulizer communicates with outer air (air injection state). When the nebulizer is controlled into the liquid injection state, the pH adjusting liquid in the adjusting liquid bottle can be sent to the nebulizer, so as to be injected from the injection port. When the nebulizer is controlled into the air injection state, bubbles of the pH adjusting liquid, which are generated in the nebulizer, can be extruded by the air, so as to be injected from the injection port of the nebulizer together with the pH adjusting liquid remaining in the nebulizer. Therefore, it is possible to suppress that a large amount of bubbles of the pH adjusting liquid are generated in the nebulizer. Therefore, the pH adjustment can be stably performed.

In the second aspect of the present invention, the communication state of the multi-way valve is switched by comparing the target intensity ratio calculated on the basis of the intensity of light of the reference wavelength with the calculated intensity ratio. Therefore, the influence of non-uniformity of the container, and the influence of the difference in the installation position of the container can be minimized, and hence the pH adjustment of the sample can be stably performed.

In the third aspect of the present invention, when the ratio of the calculated intensity ratio with respect to the target intensity ratio is within a predetermined range including 1, the period of the liquid injection state is shortened as the ratio approaches 1, and hence the injection amount of the pH adjusting liquid can be reduced as the pH of the sample approaches the target pH. Therefore, the pH of the sample can be adjusted to the target pH.

BRIEF DESCRIPTION OF DRAWINGS

FIG. 1 is a schematic view showing a configuration of an automatic pH adjustment device of a present embodiment.

FIG. 2 is an enlarged schematic view of the nebulizer 28.

FIG. 3(*a*) and (*b*) are views for explaining the operation of the three-way valve 40.

FIG. 4 is a flow chart showing a pH adjustment processing routine performed in the PC 42 in the present embodiment.

DESCRIPTION OF EMBODIMENT

In the following, an embodiment according to the present invention will be described with reference to the drawings of FIG. 1 to FIG. 4 and an experimental example.

[Configuration of Automatic pH Adjustment Device]

FIG. 1 is a schematic view showing a configuration of an automatic pH adjustment device of a present embodiment. An automatic pH adjustment device 10 of the present embodiment is a device for automatically adjusting pH of a liquid sample 12 having a pH indicator (methyl yellow, methyl orange or methyl red) added thereto. As shown in FIG. 1, the automatic pH adjustment device 10 includes a container 14 configured by a quadrangular main body section 14*a* capable of accommodating the sample 12, and an opening section 14*b* for taking in and out the sample 12. The container 14 is a transparent container made of polypropylene. However, the material of the container 14 is not limited in particular as long as the material exhibits high permeability for both light having a specific wavelength $\lambda_a$ and light having a reference wavelength $\lambda_r$, which are described below.

The main body section 14*a* is installed on a stirrer 16. A stirring bar 18 is installed in the inside of the main body section 14*a*. The stirrer 16 is configured such that the stirring bar 18 is rotated at low speed by an electromagnetic coil. The sample 12 can be gently stirred by the stirring bar 18 being rotated at low speed. It should be noted that the stirring bar 18 is not limited in particular as long as the stirring bar 18 is formed in a shape and made of a material so as to prevent that, while being rotated, the stirring bar 18 wears due to contact with the main body section 14*a*.

A light source 20 generating light having the specific wavelength $\lambda_a$ and light having the reference wavelength $\lambda_r$, and a pinhole plate 22 are installed on one side surface of the main body section 14*a*. As the light source 20, a light source, for example, such as a LED light source, a halogen light source, and a tungsten lamp, is adopted. A pinhole 22*a*, which transmits a part of a light flux emitted from the light source 20, is provided at the center of the pinhole plate 22.

A pinhole plate 24 having a pinhole 24*a* at the center thereof, and a spectroscope 26 for measuring signal intensity $I_a$ of the specific wavelength light and signal intensity $I_r$ of the reference wavelength light are installed on the other side surface of the main body section 14*a*. Instead of the spectroscope 26, it is possible to use a photodiode, an optical sensor, or the like, which has sufficient sensitivity for detecting the specific wavelength light and the reference wavelength light that are described above.

Further, the automatic pH adjustment device 10 includes a sprayer (nebulizer) 28 capable of injecting aqua ammonia 36. The nebulizer 28 is attached to a height adjustment member (not shown) and is inserted into the main body section 14*a* from the side of the opening section 14*b*. The height of an injection port 28*a* of the nebulizer 28 is adjusted so as not to be in contact with the liquid surface of the sample 12.

The configuration of the nebulizer 28 will be described with reference to FIG. 2. FIG. 2 is an enlarged schematic view of the nebulizer 28. As shown in FIG. 2, the nebulizer 28 includes a gas supply pipe 30 capable of allowing nitrogen gas as a carrier gas to flow therethrough, and a liquid supply pipe 32 capable of allowing the aqua ammonia 36 to flow therethrough. The gas supply pipe 30 includes a gas supplying port 30*a* and a gas injection port 30*b*. The gas supplying port 30*a* is connected to a compressor (not shown) which compresses and discharges nitrogen gas. The liquid supply pipe 32 includes a liquid supply port 32*a* and a liquid injection port 32*b*. The liquid supply port 32*a* is connected to a non-metallic tube 34. It should be noted that FIG. 2 shows a coaxial type nebulizer having a double pipe construction in which the liquid supply pipe 32 is arranged on the inside of the gas supply pipe 30. In addition to this type nebulizer, it is possible to use a coaxial type nebulizer having a multiple tube configuration, or a cross-flow type nebulizer characterized by fine spraying.

Again returning to FIG. 1, the configuration of the automatic pH adjustment device 10 will be described. The nebulizer 28 is connected, via the tube 34, to an adjusting liquid bottle 38 having therein the aqua ammonia 36 as a pH adjusting liquid. An electromagnetic multi-way valve (three-way valve) 40 is provided in the middle of the tube 34. The three-way valve 40 includes an internal passage 40a and an outer air communication pipe 40b.

Figure 3:
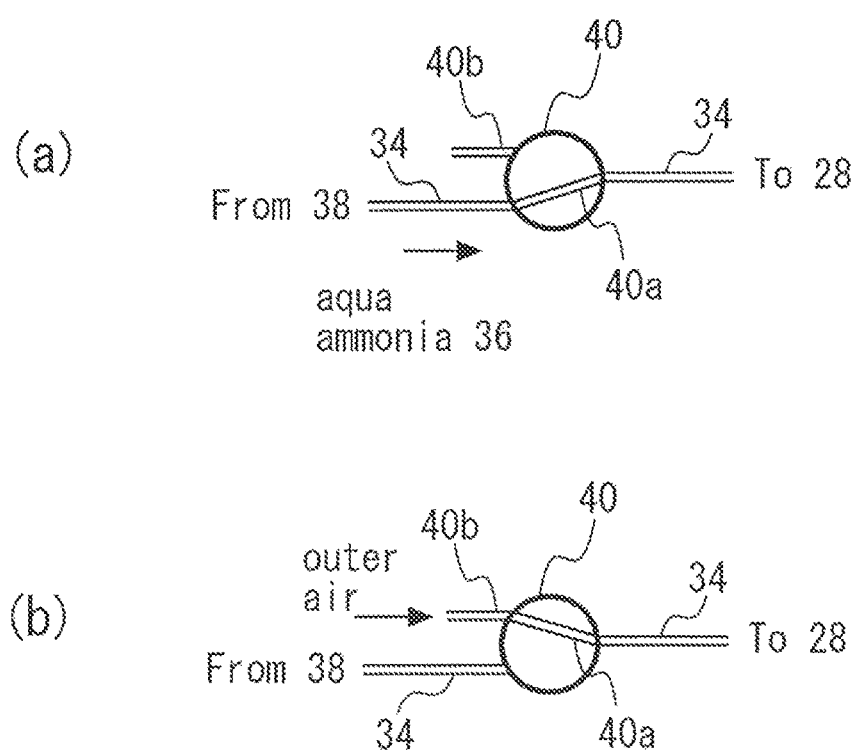

FIG. 3(a) and (b) are views for explaining the operation of the three-way valve 40. As shown in FIG. 3(a), when the internal passage 40a is operated at the side of the adjustment liquid bottle 38, the nebulizer 28 is allowed to communicate with the adjustment liquid bottle 38 (opened state). On the other hand, as shown in FIG. 3(b), when the internal passage 40a is operated at the side of the outer air communication pipe 40b, the nebulizer 28 is allowed to communicate with the outer air (closed state).

When the carrier gas is discharged from the gas injection port 30b, a negative pressure action is generated. Therefore, when the three-way valve 40 is in the opened state, the aqua ammonia 36 in the adjusting liquid bottle 38 is pulled into the internal passage 40a so as to be sent to the nebulizer 28. When the three-way valve 40 is in the closed state, air on the side of the outer air communication pipe 40b is pulled into the internal passage 40a so as to be sent to the nebulizer 28. The aqua ammonia 36 or the air sent to the nebulizer 28 is injected together with the nitrogen gas. However, the aqua ammonia 36 injected from the liquid injection port 32b collides with the gas injection port 30b to become fine droplets, and hence the atomized aqua ammonia 36 is injected onto the liquid surface of the sample 12.

Further, the automatic pH adjustment device 10 is provided with a PC 42 as a control device. The spectroscope 26 is connected to the input side of the PC 42, and a transmitted light signal 44 is inputted into the PC 42 from the spectroscope 26. On the other hand, the three-way valve 40 is connected to the output side of the PC 42 via an I/O board 46, and an opening/closing signal 48 from the PC 42 is inputted into the three-way valve 40. Similarly to the three-way valve 40, the stirrer 16 and the above-described height adjustment member may be connected to the output side of the PC 42. Further, instead of the PC 42 and the I/O board 46, a substrate integrated controller may also be used.

The PC 42 is configured to calculate a pH adjustment reaching ratio f (described below) on the basis of the transmitted light signal 44, and outputs the opening/closing signal 48 in accordance with the reaching ratio f to control the opening and closing states of the three-way valve 40. It should be noted that various calculation models, maps, and the like, are stored beforehand in an internal memory of the PC 42. For example, an algorithm for calculating the reaching ratio f, a signal intensity map representing the correlation between pH and signal intensity I, and the like are stored in the internal memory of the PC 42. It should be noted that, for example, the signal intensity map is created in such a manner that light having a predetermined wavelength is radiated to the sample with known pH, and then the correlation is obtained by measuring the intensity of the predetermined wavelength of light passing through the sample.

[Feature of Automatic pH Adjustment Device]

As described above, when the aqua ammonia as a pH adjusting liquid is injected from the nebulizer, bubbles of ammonia are generated in the nebulizer. To cope with this, the present embodiment is configured such that the operation of the three-way valve 40 is performed in accordance with the reaching ratio f. The reaching ratio $f_i$ is expressed by a ratio of a present value $R_i$ of the signal intensity ratio with respect to a target value $R_0$ of the signal intensity ratio. The present value $R_i$ is expressed by a ratio of a signal intensity $I_a$ of a specific wavelength with respect to a signal intensity $I_r$ of a reference wavelength.

Figure 4:
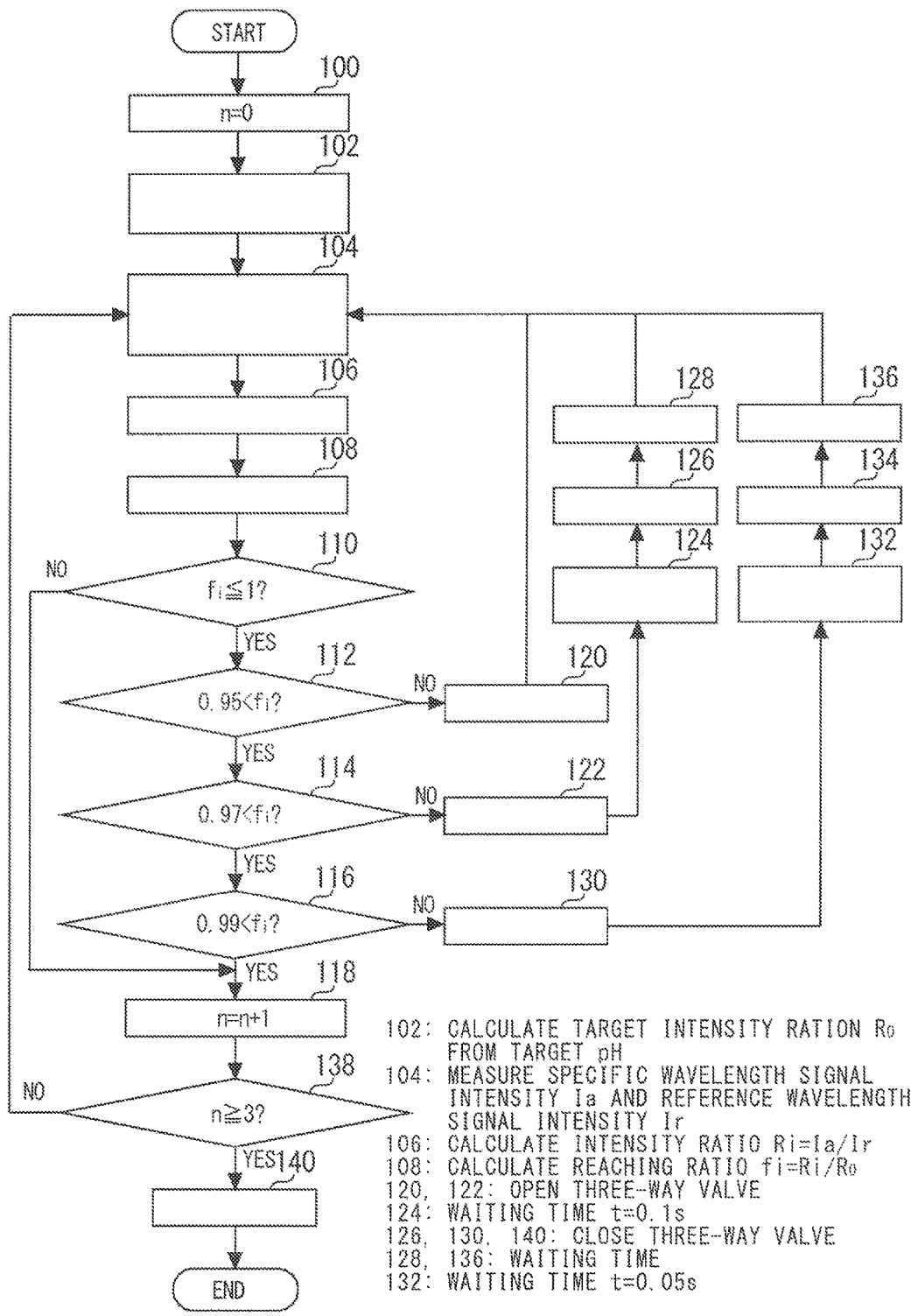

FIG. 4 is a flow chart showing a pH adjustment processing routine performed in the PC 42 in the present embodiment. It should be noted that it is assumed that, at the time of the start of the processing routine in the present embodiment, the target pH, the specific wavelength $\lambda_a$, and the reference wavelength $\lambda_r$ are determined in accordance with color change characteristics of a pH indicator and are inputted into the PC 42. Further, it is assumed that, at the time of the start of the processing routine, the three-way valve 40 is controlled to be in the closed state.

In the routine shown in FIG. 4, first, the value of the number of repetitions n is set to zero (step 100). The number of repetitions n is counted each time the reaching ratio f is measured once. When the process in step 100 is processed, the count number at the time of the previous adjustment is reset.

Next, the target value $R_0$ of the signal intensity ratio is calculated from the target pH (step 102). Specifically, first, a map corresponding to the target pH is searched among the signal intensity maps described above, and signal intensities $I_{a0}$ and $I_{r0}$ respectively corresponding to the specific wavelength $\lambda_a$ and the reference wavelength $\lambda_r$ are calculated. Then, the target value $R_0$ is calculated by dividing the signal strength $I_{a0}$ by the signal strength $I_{r0}$.

Next, the signal intensities $I_a$ and $I_r$ are measured (step 104). Specifically, the measurement of the signal intensities $I_a$ and $I_r$ is performed by alternately radiating light of the specific wavelength $\lambda_a$ and light of the reference wavelength $\lambda_r$ from the light source 20. The signal intensity $I_a$ is measured on the basis of the transmitted light signal 44 which is inputted into the PC 42 from the spectroscope 26 during the radiation of the specific wavelength light. The signal intensity $I_r$ is measured on the basis of the transmitted light signal 44 which is inputted into the PC 42 from the spectroscope 26 during the radiation of the reference wavelength light.

Next, the present value $R_i$ of the signal intensity ratio is calculated (step 106). Specifically, the present value $R_i$ is calculated by dividing the signal intensity $I_a$ measured in step 104 by the signal intensity $I_r$ measured in step 104.

Next, the reaching ratio $f_i$ is calculated (step 108). Specifically, the reaching ratio $f_i$ is calculated by dividing the present value $R_i$ calculated in step 106 by the target value RO calculated in step 102.

Next, the reaching ratio $f_i$ is evaluated. (step 110 to step 136). Specifically, first, it is determined whether or not the reaching ratio $f_i \leq 1$ is established (step 110). When it is determined that the reaching ratio $f_i \leq 1$ is established, it is determined whether or not 0.95<the reaching ratio $f_i$ is established (step 112). When it is determined that 0.95<the reaching ratio $f_i$ is established, it is determined whether or not 0.97<the reaching ratio $f_i$ is established (step 114). When it is determined that 0.97<the reaching ratio $f_i$ is established, it is determined whether or not 0.99<the reaching ratio $f_i$ is established (step 116). When it is determined that 0.99<the reaching ratio $f_i$ is established, the number of repetitions is counted (step 118).

When, in step 110, it is determined that the reaching ratio $f_i \leq 1$ is not established, the process proceeds to step 118. When, in step 112, it is determined that 0.95<the reaching ratio $f_i$ is not established, the three-way valve 40 is controlled to be in the opened state (step 120). Thereby, the aqua ammonia 36 in the adjusting liquid bottle 38 is sent to the nebulizer 28, so as to be injected from the liquid injection port 32b. After the process in step 120, the process returns to step 104, and the signal intensities $I_a$ and $I_r$ are measured.

That is, the process returning from step 120 to step 104 is repeated until 0.95<the reaching ratio $f_i$ is established.

When, in step 114, it is determined that 0.97<reaching ratio $f_i$ is not established, the three-way valve 40 is controlled to be in the opened state (step 122), and a waiting time (0.1 second) is measured (step 124). Thereby, until the waiting time elapses, the aqua ammonia 36 in the adjusting liquid bottle 38 is sent to the nebulizer 28 and is injected from the liquid injection port 32b. After the elapse of the waiting time, the three-way valve 40 is controlled to be in the closed state (step 126), and a waiting time is again measured (step 128). Thereby, until the waiting time elapses, air on the side of the outer air communication pipe 40b is sent to the nebulizer 28 and is injected from the liquid injection port 32b together with the aqua ammonia remaining in the nebulizer 28. After the process of this step, the process returns to step 104, and the signal intensities $I_a$ and $I_r$ are measured. That is, the process, which returns from step 114 to step 104 through steps 122, 124, 126 and 128, is repeatedly performed until 0.97<reaching ratio $f_i$ is established.

When, in step 116, it is determined that 0.99<reaching ratio $f_i$ is not established, the three-way valve 40 is controlled to be in the opened state (step 130), and a waiting time (0.05 second) is measured (step 132). After the elapse of the waiting time, the three-way valve 40 is controlled to be in the closed state (step 134). The process of steps 130, 132 and 134 is basically the same as the process of steps 122, 124 and 126. However, the waiting time of step 132 is set to be shorter than the waiting time of step 124. After the process of step 134, a waiting time is again measured (step 136). The waiting time of step 136 is set to be the same as the waiting time of step 128. After the process of step 136, the process returns to step 104, and the signal intensities $I_a$ and $I_r$ are measured. That is, the process which returns from step 116 to step 104 through steps 130, 132, 134 and 136 is repeatedly performed until 0.99<reaching ratio $f_i$ is established.

Subsequently to step 118, it is determined whether or not the number of repetitions n≥3 is established (step 138). When the determination in step 138 is performed, the accuracy of the determination of steps 110 to 116 is ensured. When it is determined that the number of repetitions n<3 is established, the process returns to step 104, and the signal intensities $I_a$ and $I_r$ are measured. When it is determined that the number of repetitions n≥3 is established, the three-way valve 40 is controlled to be in the closed state (step 140). Thereby, the pH adjustment is ended.

As described above, in the routine shown in FIG. 4, when the process of step 128 or step 136 is performed, bubbles of ammonia, which are generated in the nebulizer 28, can be extruded by air so as to be injected from the injection port 28a together with the aqua ammonia remaining in the nebulizer 28. Therefore, it is possible to perform the pH adjustment while suppressing the generation of bubbles of ammonia in the nebulizer 28. Therefore, the pH adjustment of the sample 12 can be continuously performed. Further, the waiting time of step 132 is set to be shorter than the waiting time of step 124, and hence the injection amount of the aqua ammonia can be reduced as the reaching ratio $f_i$ approaches 1.00. Therefore, pH of the sample 12 can be adjusted to the target pH. Further, when the determination is performed in step 138, the accuracy of the determination in step 110 to step 116 can be ensure. Therefore, the pH adjustment of the sample 12 can be performed with high accuracy.

In addition, with the routine shown in FIG. 4, the reaching ratio $f_i$ used for the determination in each of step 110 to step 116 can be calculated on the basis of the signal intensities ratios $R_a$ and $R_r$. Therefore, the influence due to the non-uniformity of the container 14, and the influence due to the difference in the installation position of the container 14 can be minimized, and hence the pH adjustment of the sample 12 can also be stably performed.

Meanwhile, in the present embodiment, the aqua ammonia is used as the pH adjusting liquid, but carbonated water, having a property of not including a metallic component and a property of generating bubbles in a pressure reduction state, may also be used similarly to the aqua ammonia.

Further, in the present embodiment, the signal intensities $I_{a0}$ and $I_{r0}$ are calculated by using the signal intensity map representing a correlation between pH and the signal intensity I, and the target value $R_0$ of the signal intensity ratio is calculated from the signal intensities $I_{a0}$ and $I_{r0}$. However, the target value $R_0$ may also be directly calculated by using the signal intensity ratio map representing a correlation between pH and the signal intensity ratio R. It should be noted that, similarly to the signal intensity map, the signal intensity ratio map can be created by obtaining the correlation between pH and the signal intensity ratio R.

Further, in the present embodiment, the range of the reaching ratio $f_i$ is set into three stages as shown in steps 112, 114 and 116, but the range of the reaching ratio $f_i$ may be set into four or more steps. Also in this case, as shown in step 124 and 126, when the waiting time is shortened as the reaching ratio $f_i$ approaches 1.00, the injection amount of the aqua ammonia can be reduced as pH of the sample 12 approaches the target pH. Therefore, pH of the sample 12 can be adjusted to the target pH.

Experimental Example

Next, the automatic pH adjustment device of the present embodiment will be further described with reference to an experimental example.

Test sample: a methyl red indicator (0.1%) and acetic acid (99%) of 0.5 ml are added into a 0.7% nitric acid solution of 50 ml, and the pH adjustment was performed by using aqua ammonia (28%). The specific wavelength $\lambda_a$ was set to 550 nm, and the reference wavelength $\lambda_r$ was set to 650 nm.

Result: the signal intensity of light of the specific wavelength $\lambda_a$, and the signal intensity of light of the reference wavelength $\lambda_r$ change simultaneously, and hence the pH adjustment could be stably performed even when the installation position of the container 14 was changed. When the pH adjustment was performed by setting the adjustment target as pH=6.0, eight independent test samples were divided into three groups of one test sample having pH=5.9, and five test samples having pH=6.0, and two test samples having pH=6.1. The adjustment of each of the test samples could be completed within five minutes.

From this result, it was confirmed that the pH adjustment can be performed with sufficient accuracy to ensure the reproducibility of the recovery ratio of trace elements in solid-phase extraction.

DESCRIPTION OF REFERENCE NUMERALS

10 Automatic pH adjustment device
12 Sample
14 Container
20 Light source
26 Spectroscope
28 Nebulizer
28a Injection port 36 Aqua ammonia
38 Adjusting liquid bottle
40 Three-way valve
42 PC
44 Transmitted light signal
50 Opening/closing signal.

The invention claimed is:

1. An automatic pH adjustment device comprising:
a container configured to accommodate a liquid sample to which a pH indicator is added, color of the pH indicator changes in accordance with pH;
an adjusting liquid bottle configured to store aqua ammonia or carbonated water used as a pH adjusting liquid;
a nebulizer that is provided with an injection port disposed to face a sample liquid surface in the container and is configured to inject from the injection port the pH adjusting liquid stored in the adjusting liquid bottle and atomized by a carrier gas;
a multi-way valve that is disposed between the nebulizer and the adjusting liquid bottle and is configured to switch between a liquid injection state in which the nebulizer is allowed to communicate with the adjusting liquid bottle to inject the pH adjusting liquid from the injection port, and an air injection state in which the nebulizer is allowed to communicate with outer air to inject air from the injection port;
a detecting device configured to detect the intensity of light radiated from the outside of the container and transmitted through the container; and
a control device configured to switch the communication state of the multi-way valve on the basis of the intensity of light detected by the detecting device, wherein
the detecting device is configured to detect the intensity of light of a specific wavelength absorbed by the pH indicator if the sample is adjusted to target pH and the intensity of light of a reference wavelength not absorbed by the pH indicator if the sample is adjusted to the target pH; and
the control device is configured to calculate an intensity ratio from the intensity of light of the specific wavelength detected by the detection device and the intensity of light of the reference wavelength detected by the detection device, and is configured to switch the communication state of the multi-way valve after comparing the calculated intensity ratio with a target intensity ratio set in accordance with the target pH.

2. The automatic pH adjustment device according to claim 1, wherein the control device is also configured to reduce the period of the liquid injection state as the ratio approaches 1, when the ratio of the calculated intensity ratio with respect to the target intensity ratio is in a predetermined range including 1.

* * * * *